(12) United States Patent
Murugesan et al.

(10) Patent No.: US 10,480,313 B2
(45) Date of Patent: Nov. 19, 2019

(54) MULTICOLOR FLUORESCENT SILICA NANOPARTICLES AS TRACERS FOR PRODUCTION AND WELL MONITORING

(71) Applicants: Sankaran Murugesan, Katy, TX (US); Radhika Suresh, Sugar Land, TX (US); Oleksandr Kuznetsov, Manvel, TX (US); Valery Khabashesku, Houston, TX (US); Qusai Darugar, Houston, TX (US)

(72) Inventors: Sankaran Murugesan, Katy, TX (US); Radhika Suresh, Sugar Land, TX (US); Oleksandr Kuznetsov, Manvel, TX (US); Valery Khabashesku, Houston, TX (US); Qusai Darugar, Houston, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 165 days.

(21) Appl. No.: 15/626,389

(22) Filed: Jun. 19, 2017

(65) Prior Publication Data

US 2018/0363452 A1 Dec. 20, 2018

(51) Int. Cl.
*E21B 47/10* (2012.01)
*B82Y 15/00* (2011.01)
(Continued)

(52) U.S. Cl.
CPC .......... *E21B 47/1015* (2013.01); *B82Y 15/00* (2013.01); *C09K 8/032* (2013.01);
(Continued)

(58) Field of Classification Search
CPC .. E21B 47/1015; E21B 43/267; E21B 47/102; E21B 49/085; B82Y 15/00;
(Continued)

(56) References Cited

U.S. PATENT DOCUMENTS

| | | | | |
|---|---|---|---|---|
| 5,686,724 A | * | 11/1997 | Spilker | E21B 49/005 250/255 |
| 2012/0004776 A1 | * | 1/2012 | Abad | C09K 8/03 700/265 |

(Continued)

FOREIGN PATENT DOCUMENTS

WO 2012091599 A1 7/2012

OTHER PUBLICATIONS

Al-Abbad, et al. "A Step-Change for Single Well Chemical Tracer Tests SWCTT: Field Pilot Testing of New Sets of Novel Tracers", SPE Annual Technical Conference and Exhibition held in Dubai, UAE, Sep. 26-28, 2016; 16 pages.

(Continued)

*Primary Examiner* — Silvana C Runyan
(74) *Attorney, Agent, or Firm* — Cantor Colburn LLP

(57) ABSTRACT

A method of determining a property within a subterranean formation comprises introducing silica nanoparticles into a well; obtaining a sample of a fluid produced from the well; and analyzing the sample for presence of the silica nanoparticles, wherein the silica nanoparticles comprise a core, a donor chromophore, an acceptor chromophore, and an outer silica shell; the donor chromophore and the acceptor chromophore being selected such that an emission spectrum of the donor chromophore overlaps with an absorption spectrum of the acceptor chromophore.

22 Claims, 8 Drawing Sheets

(51) Int. Cl.
   *G01N 33/24*   (2006.01)
   *C09K 8/03*   (2006.01)
   *C09K 8/80*   (2006.01)
   *C09K 8/035*   (2006.01)
   *C09K 8/56*   (2006.01)
   *C09K 8/58*   (2006.01)
   *C09K 8/66*   (2006.01)
   *C09K 8/72*   (2006.01)

(52) U.S. Cl.
   CPC ............... *C09K 8/035* (2013.01); *C09K 8/56* (2013.01); *C09K 8/58* (2013.01); *C09K 8/665* (2013.01); *C09K 8/72* (2013.01); *C09K 8/805* (2013.01); *G01N 33/241* (2013.01); *C09K 2208/10* (2013.01)

(58) Field of Classification Search
   CPC .......... C08K 3/36; C09K 8/032; C09K 8/805; G01N 33/241
   See application file for complete search history.

(56) References Cited

U.S. PATENT DOCUMENTS

2013/0084643 A1   4/2013   Commarieu et al.
   2015/0001385 A1   1/2015   Perriat et al.
   2016/0097750 A1   4/2016   Van Herzen et al.
   2016/0363693 A1   12/2016   Murugesan et al.
   2016/0369157 A1   12/2016   Agrawal et al.
   2017/0022804 A1   1/2017   Gupta et al.

OTHER PUBLICATIONS

Ellis, et al. "Transforming Oil Tracer Studies", SPE Kingdom of Sauda Arabia Technical Symposium and Exhibition held in Dammam, Saudi Arabia, Apr. 25-26, 2016; 14 pages.

Kosynkin, et al. "Oil Industry Interwell Trial of Reservoir Nanoagent Tracers", SPE Annual Technical Conference and Exhibition held in Dubai, UAE, Sep. 26-28, 2016; 15 pages.

Sanni, et al. "A Field Case Study of Inter-well Chemical Tracer Test", SPE International Symposium on Oilfield chemistry held in the Woodlands, TX, USA, Apr. 13-15, 2015; 17 pages.

Xu, et al. "Multicolor Dye-Doped Silica Nanoparticles Independent of FRET", State Key Labratory of Supramolecular Structure and Materials, College of Chemistry, Jilin University, Changchun 130012, People's Republic of China, 2010; 4 pages.

Zaberi, et al. "Improved Reservoir Surveillance through Injected Tracers in a Saudi Arabian Oil Field: Case Study", SPE Reservoir Characterization and Simulation Conference and Exhbition held in Abu Dhabi, UAE, Sep. 16-18, 2013; 15 pages.

Ren, T. "Synthesis and Spectroscopic Properties of Silica-Dye-Semiconductor Nanocrystal Hybrid Particles", Langmuir 2010, 26(23), 17981-17988.

International Search Report, International Application No. PCT/US2018/032296, Korean Intellectual Property Office; International Search Report 3 pages.

International Written Opinion, International Application No. PCT/US2018/032296, Korean Intellectual Property Office; International Written Opinion 11 pages.

\* cited by examiner

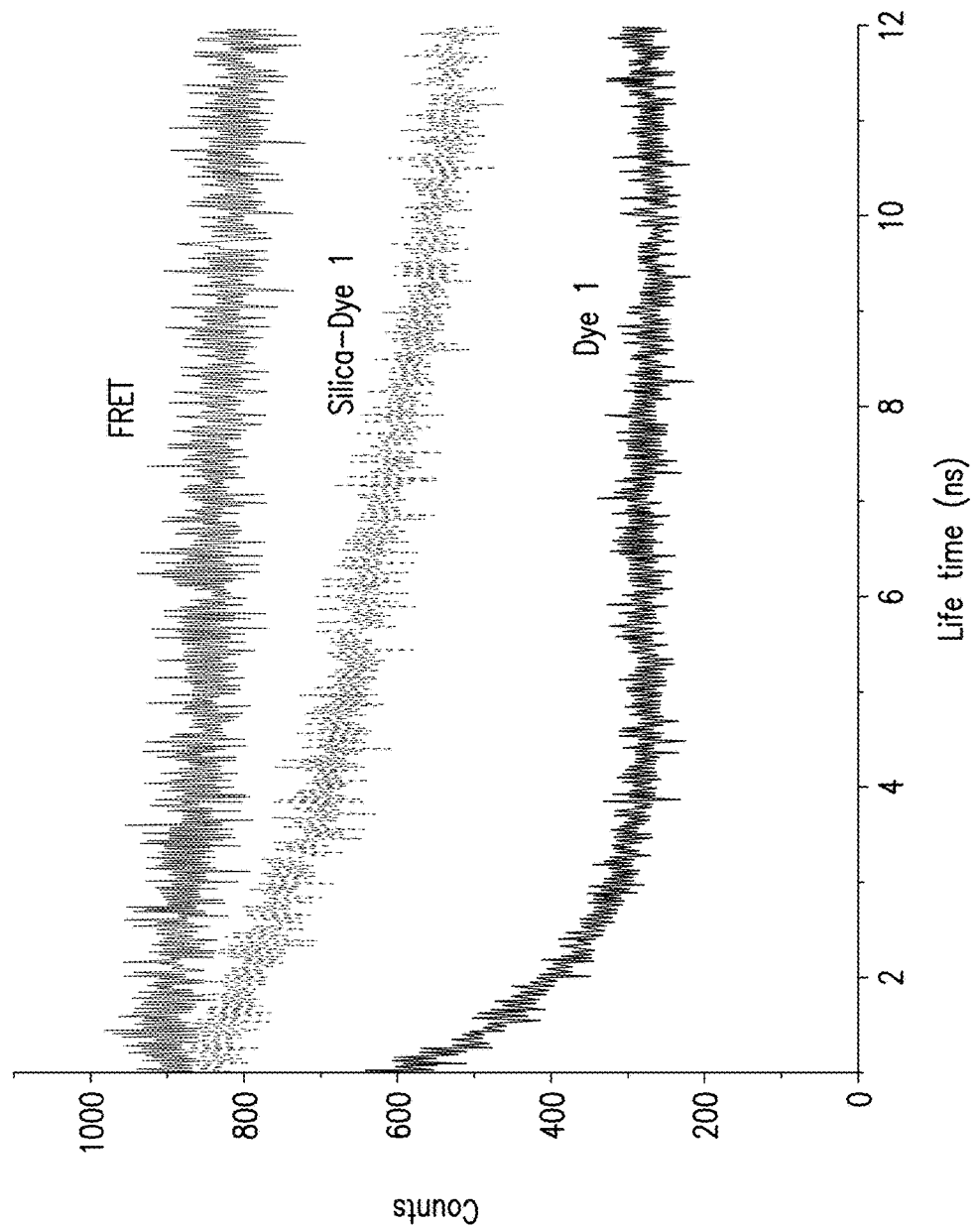

US 10,480,313 B2

MULTICOLOR FLUORESCENT SILICA NANOPARTICLES AS TRACERS FOR PRODUCTION AND WELL MONITORING

BACKGROUND

Tracers have been used in the oil and gas industry to provide valuable reservoir information such as inter-well connections, heterogenetities, and water movements. Tracers can also be used in reservoir monitoring. Reservoir monitoring refers to the gathering and analysis of information from reservoirs during production. Such monitoring is used to assess the productivity of producing formations or zones within the formations from which fluids are being produced. Monitoring of produced fluids is important in order to increase efficiency of a hydraulic fracturing operation. Reservoir monitoring is further used to determine water saturation levels in the well.

Tracers may include radioactive elements and stable isotopes, chemicals, such as fluorescent dyes, and inorganic ions. However, certain radioactive elements are not environmentally friendly. Inorganic ions may require long detection times. Dyes are susceptible to decomposition under harsh conditions. Accordingly the industry is always receptive to alternative tracers and improved methods for reservoir monitoring and evaluation.

BRIEF DESCRIPTION

In an embodiment, silica nanoparticles comprise a core, a donor chromophore, an acceptor chromophore, and an outer silica shell; the donor chromophore and the acceptor chromophore being selected such that an emission spectrum of the donor chromophore overlaps with an absorption spectrum of the acceptor chromophore. The silica nanoparticles can be used as a tracer for various downhole applications.

A method of determining a property within a subterranean formation comprises introducing silica nanoparticles into a well; obtaining a sample of a fluid produced from the well; and analyzing the sample for presence of the silica nanoparticles.

A method of fracturing multiple productive zones of a subterranean formation penetrated by a well comprises injecting a fracturing fluid into the multiple production zones at a pressure sufficient to enlarge or create fractures in the multiple productive zones, wherein the fracturing fluid comprises silica nanoparticles; recovering a fluid containing hydrocarbons from one or more of the multiple productive zones; detecting the silica nanoparticles in the recovered fluid; and identifying the zone from which the recovered fluid was produced or monitoring an amount of fluids produced from at least one of the multiple productive zones by identifying the silica nanoparticles in the recovered fluid.

A method of enhancing the production of hydrocarbon from a production well penetration a hydrocarbon bearing formation, wherein one or more of the injection well are associated with the production well, the method comprises: introducing into one or more of the injection wells a fluid comprising silica nanoparticles; flowing at least a portion of the fluid comprising the silica nanoparticles from the injection well to the production well; and recovering a production fluid from the production well.

A method of determining water breakthrough in a production well associated with one or more injection wells comprises: introducing a fluid comprising silica nanoparticles into an injection well; flowing the fluid from the injection well into the production well; producing a production fluid from the production well; determining water breakthrough in the production well by qualitatively determining the presence or quantitatively measuring the amount of the silica nanoparticles in the production fluid.

A method of increasing hydrocarbon production from a production well penetrating a hydrocarbon-bearing reservoir, wherein more than one injection well is associated with the production well, comprises injecting a fluid comprising silica nanoparticles into the more than one injection well, the fluid pumped into each of the injection wells comprising qualitatively distinguishable silica nanoparticles; identifying, upon water breakthrough in the production well, the injection well into which the breakthrough water was injected by qualitatively determining the presence of silica nanoparticles in a fluid recovered from the production well; and shutting off the identified injection well.

BRIEF DESCRIPTION OF THE DRAWINGS

The following descriptions should not be considered limiting in any way. With reference to the accompanying drawings, like elements are numbered alike:

FIG. 14 shows time correlated single photon counting lifetime measurement of pure dye-1, silica-dye-1 and FRET-silica.

DETAILED DESCRIPTION

The inventors have discovered that some of the challenges associated with current chemical or dye based tracers such as thermal degradation over time, phase separation, and tedious detection processes, can be addressed by using environmentally friendly silica nanoparticles. The silica nanoparticles are stable at elevated temperatures for an extended period of time, and can be used as a tracer for various downhole applications.

The silica nanoparticles comprise a core, a donor chromophore, an acceptor chromophore, and an outer silica shell. The core can be silica. The donor chromophore or the acceptor chromophore are doped on the core via coating, adsorption, absorption, covalent bonding, or a combination comprising at least one of the foregoing. In an embodiment, the core is functionalized first, and the donor chromophore or acceptor chromophore are covalently bonded to the core via a functional group on the core.

The silica nanoparticles can further comprise an intermediate silica shell (also referred to as intermediate silica layer) separating the donor and acceptor chromophores. For example, an intermediate silica shell can encapsulate the core doped with a donor chromophore. The intermediate silica shell can then be doped with an acceptor chromophore via coating, adsorption, absorption, covalent bonding, or a combination comprising at least one of the foregoing.

Figure 1:
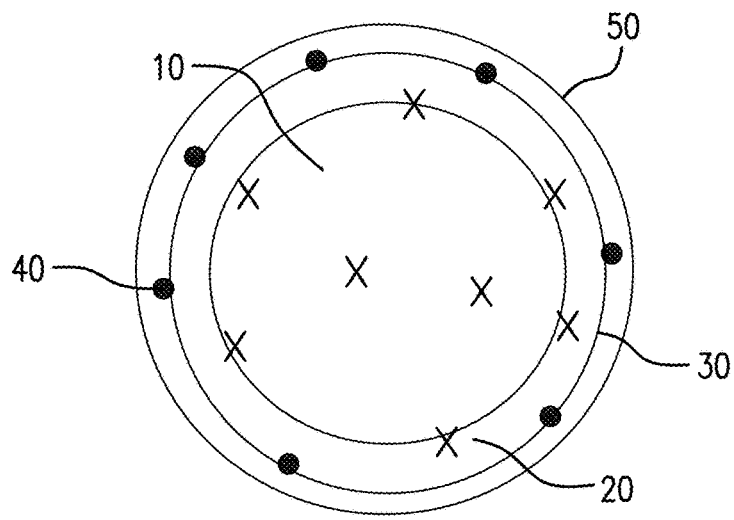
FIG. 1 is a schematic diagram illustrating an exemplary structure of multicolored silica nanoparticles according to an embodiment of the disclosure.

FIG. 1 is a schematic diagram illustrating an exemplary structure of multicolored silica nanoparticles according to an embodiment of the disclosure. As shown in FIG. 1, silica nanoparticles include a core 10, a donor chromophore 20, an intermediate silica shell 30, an acceptor chromophore 40, and an outer silica shell 50. It is appreciated that the chromophore 20 can be an acceptor chromophore and the chromophore 40 can be a donor chromophore.

Figure 2:
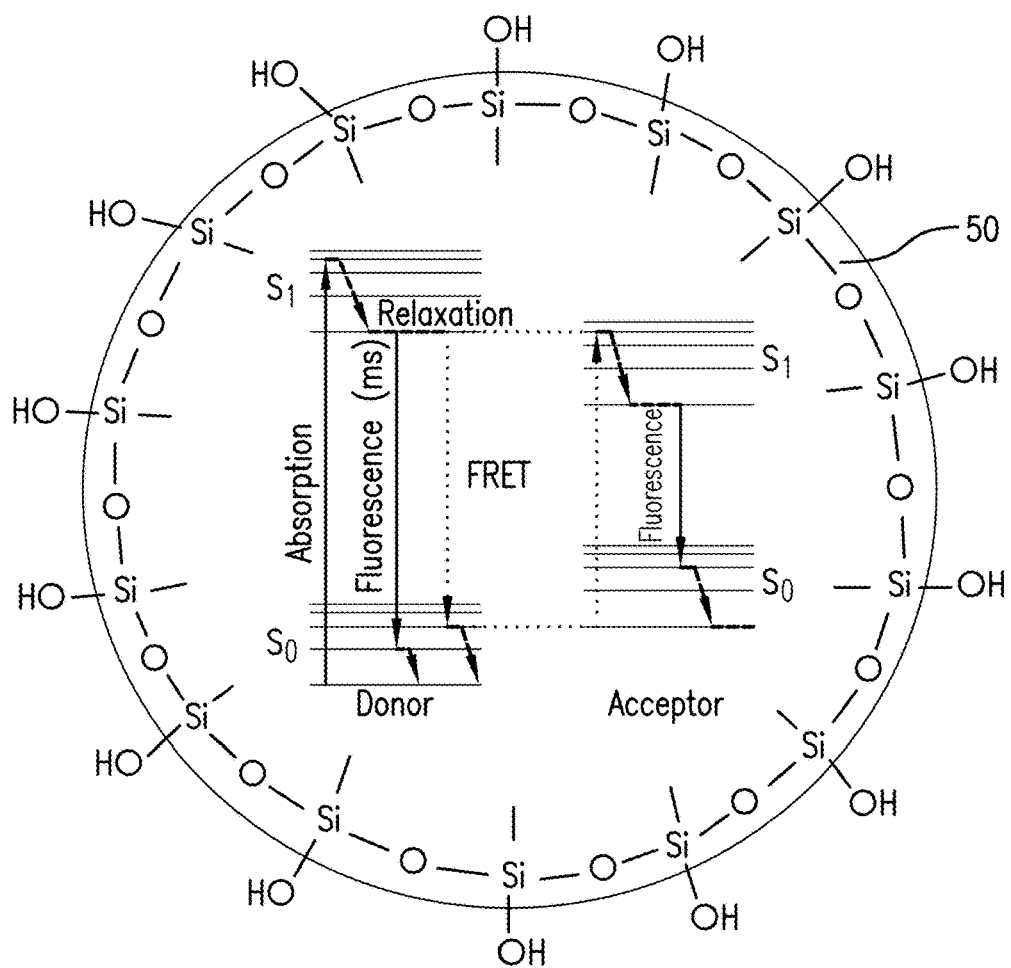
FIG. 2 is a schematic representation showing the scientific phenomena of multicolor silica particles.

The silica nanoparticles can have multicolors, which is achieved by utilizing the concept of FRET (Förster resonance energy transfer or fluorescence resonance energy transfer) as illustrated in FIG. 2. FRET is a mechanism describing energy transfer between two light-sensitive molecules. A donor chromophore, initially in its electronic excited state, may transfer energy to an acceptor chromophore through nonradiative dipole-dipole coupling. By tuning the composition and concentration of the acceptor chromophore and utilizing the energy transfer from the donor chromatophors to the acceptor chromatophors, multiple colors of silica nanoparticles are generated. The silica component plays an important role in enhancing the quantum efficacy of the fluorescence energy transfer process. The lifetime of the system is also increased by the presence of silica. Moreover, the silica component greatly improves the stability of the donor and acceptor chromatophors at high temperatures allowing the nanoparticles to be used under harsh downhole conditions.

The donor chromophore and the acceptor chromophore are selected such that an emission spectrum of the donor chromophore overlaps with an absorption spectrum of the acceptor chromophore. In an embodiment, the donor chromophore is a fluorescent and the acceptor chromophore is a fluorescent or phosphorescent. Specific examples of the donor and acceptor chromophores include fluorescein isothiocyanate and tris(1,10-phenanathroline) ruthenium respectively. The amount of the donor chromophore is about 0.1 micro moles to about 10 milli moles or about 1 micro moles to about 10 milli moles, based on 1 g of silica core particles. The amount of the acceptor chromophore is about 0.001 micromoles to about 10 milli moles or about 0.01 micro moles to about 10 milli moles, based on 1 g of silica core particles. Minimum detectable amount for an individual nanoparticle is in the range of 5 to 10 pico molar concentrations of both acceptor and donor chromophore.

Figure 3:
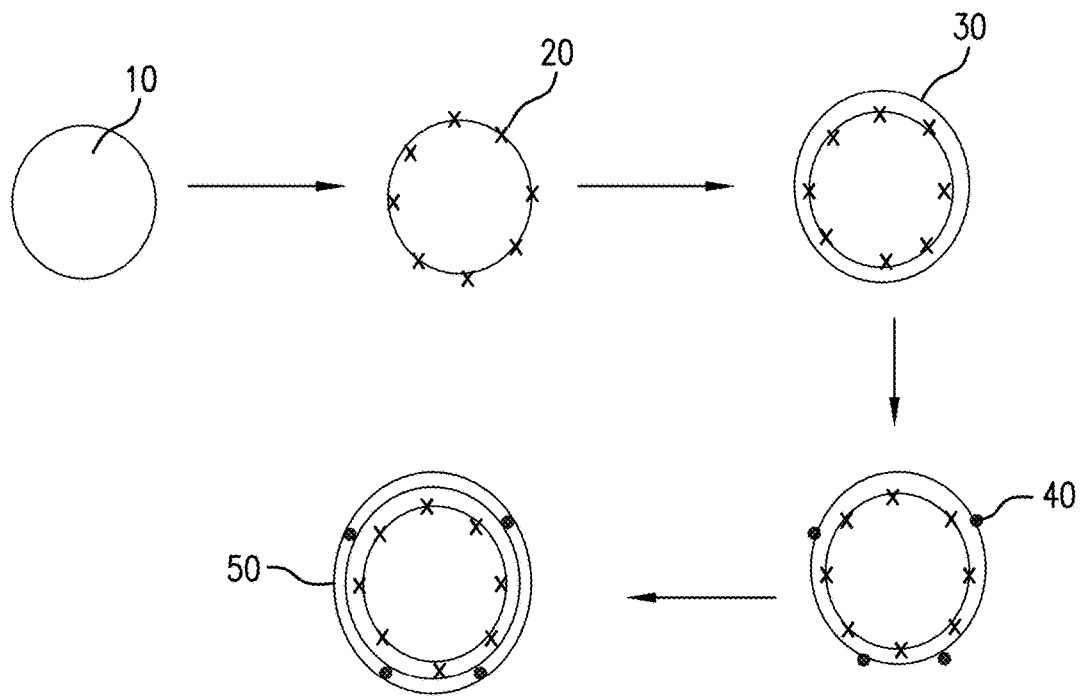
FIG. 3 is a schematic representation of the synthesis of silica nanoparticles according to an embodiment of the disclosure.

The silica nanoparticles can be formed via a stepwise process as illustrated in FIG. 3. As shown in FIG. 3, core particle 10 or functionalized core particle 10 is treated with a donor or acceptor chromophore 20 to obtain a donor or acceptor doped particle. Then a layer of silica is deposited or coated on the doped particle. In an embodiment, an intermediate silica shell 30 is grown on the surface of the doped particle by treating the doped particle with tetraethyl ortho silicate, ammonia, and water. The particle having the intermediate silica shell is then doped with an acceptor or donor chromophore 40. Another layer of silica is deposited or coated on the particle having the donor and acceptor chromophore. In an embodiment, an outer silica shell 50 is grown on the surface of the donor and acceptor doped particle by treating the donor and acceptor doped particle with tetraethyl ortho silicate, ammonia, and water.

The silica nanoparticles can have an average particle size of less than about 100 nm, for example about 20 to about 90 nm. The thickness of the outer silica shell and the intermediate silica shell can be in the range of about 1 nm to about 15 nm or about 1 nm to about 10 nm.

The silica nanoparticles can be non-functionalized, or can be functionalized to include chemical functional groups to increase dispersibility, reactivity, surface properties, compatibility, and other desirable properties. As used herein, "functionalized silica nanoparticles" include both non-covalently functionalized silica nanoparticles and covalently functionalized silica nanoparticles. Non-covalent functionalization is based on van der Walls forces, hydrogen bonding, ionic interactions, dipole-dipole interactions, hydrophobic or π-π interactions. Covalent functionalization means that the functional groups are covalently bonded to the silica nanoparticles, either directly or via an organic moiety.

Any known methods to functionalize silica can be used. For example, surfactants, ionic liquids, or coupling agents, or a combination comprising at least one of the foregoing can be used to functionalize the nanoparticles.

In an embodiment, silica nanoparticles is covalently functionalized with a silane coupling agent. Exemplary silane coupling agents have the formula

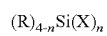

$$(R)_{4-n}Si(X)_n$$

wherein X is a hydrolysable group such as alkoxy, acryloxy, halogen, or amine; R is a nonhydrolysable organic functional group such as an alkyl group, amine, ether, or alcohol, and n is from 1 to 3. To impart oleophilic properties to silica nanoparticles, R can be a $C_{5-30}$, $C_{6-25}$, or $C_{8-20}$ alkyl group. Functional groups such as amino, hydroxyl, and ether can be coupled to the Si atom via an organic moiety such as an alkyl group. In an embodiment, the silane coupling agents are alkoxy silane such as monoalkoxy silane, dialkoxy silane, or trialkoxy silane. Trialkoxy silanes such as trimethoxy silanes and triethoxy silanes are specifically mentioned.

The outer silica shell, the silica core, and the intermediate silica shell can be functionalized. The functionalization of the outer silica shell can tune the dispersibility of the silica nanoparticles in a fluid. The functionalization of the silica core and the intermediate silica shell can tune the reactivity of the silica with the donor chromophore or acceptor chromophore.

The silica nanoparticles can be introduced into a subterranean formation penetrated by a wellbore, and by analyzing a sample of the fluid obtained from the wellbore for presence of silica nanoparticles, various properties of the subterranean formation can be obtained. As used herein, analyzing the presence of silica nanoparticles include analyzing the concentration of the silica nanoparticles. The optical properties of silica nanoparticles normally can be used to determine at least one property of the subterranean formation penetrated by a well. Exemplary optical properties include an absorption spectrum, an absorption intensity, a peak absorption wavelength, an emission spectrum, a peak emission wavelength, and a fluorescence intensity of silica nanoparticles. Methods of measuring the optical properties of silica nanoparticles are known in the art and are not particularly limited.

Exemplary properties that can be determined include a wettability of formation surfaces, a production zone within the subterranean formation, the productivity of the zones within the formation, an identification of injection well contributing to the flow of breakthrough water, flow paths through the subterranean formation, and the like. By analyzing the information and taking appropriate actions, the production of hydrocarbons can be improved.

In an embodiment, the silica nanoparticles are introduced into the subterranean formation with a fluid delivery system configured to deliver a fluid having the silica nanoparticles suspended therein to the subterranean formation.

In another embodiments, the silica nanoparticles are introduced into one or more injection wells in a fluid delivery system configured to deliver a fluid into the injection well and to maintain pressure within the wellbore above the bubble point of fluids being extracted from the formation.

Delivery fluids transporting silica nanoparticles into the formation are aqueous or non-aqueous based. Exemplary carriers include brine, such as a potassium chloride or sodium chloride brine; salt water such as seawater; fresh water; a liquid hydrocarbon; or a surfactant based fluid. The silica nanoparticles may further be injected into the formation in gas such as carbon dioxide, nitrogen and carbon dioxide/nitrogen, liquefied gas, such as liquefied natural gas or liquefied petroleum gas as well as in foams. The delivery fluid is preferably aqueous, steam or gas (water flooding, steam flooding or gas flooding).

Generally, fluids pumped into the formation, injection well, or production well do not require excessive amounts of the silica nanoparticles. The minimum amount of silica nanoparticles in the fluid introduced into the formation, the production well or injection well is that amount sufficient to permit detection within a produced fluid. Typically, the amount of silica nanoparticles present in the introduced fluid is between from about 1 ppm to about 500,000 ppm.

The silica nanoparticles may be used to identify fluids produced from the well. Since the silica nanoparticles may be detected in recovered produced fluids, the methods described herein thus do not require downhole equipment for detection. Typically, fluids transported out of the well are evaluated and the silica nanoparticles are identified on the fly or at a location distant from the wellbore.

The silica nanoparticles may be used to identify a source of fluids produced from a production well. As an example, silica nanoparticles may be introduced proximate the aquifer zone. Produced fluids may be analyzed to determine if the produced fluids include an optical property of the silica nanoparticles introduced into the aquifer zone. Identification of the corresponding optical property may be an indication that the produced fluid includes water from the aquifer zone.

Silica nanoparticles exhibiting different optical properties may be introduced into various zones of the subterranean formation to determine a location (e.g., a zone) from which produced fluids (e.g., hydrocarbons, water, etc.) originate. In some embodiments, between about one and about twenty different types of silica nanoparticles, each exhibiting one or more different optical properties than the other types of silica nanoparticles, may be introduced into one or more different zones of the subterranean formation. A produced fluid exhibiting an optical property, such as fluorescence, corresponding to a property of silica nanoparticles introduced into a zone of the subterranean zone may be an indication that the produced fluid originated from the zone in which the silica nanoparticles were introduced.

Thus, in some embodiments, silica nanoparticles exhibiting different optical properties may be introduced into multiple zones of the subterranean formation. (The term "zone" as used herein may refer to separate formations within a well or separate areas within a single formation within the well.) The silica nanoparticles introduced in one zone may be different from the silica nanoparticles introduced into another zone being treated. The silica nanoparticles introduced into different zones are preferably qualitatively (and preferably also quantitatively) distinguishable in order to identify the zone or area within the formation from which a produced fluid originates. As such, the silica nanoparticles introduced into each of the zones being treated preferably exhibit unique absorption and optical properties such that the properties of silica nanoparticles introduced into one zone is unable to mask the properties of silica nanoparticles introduced into another zone.

Detection of an optical property in a produced fluid corresponding to an optical property of silica nanoparticles disposed in a zone of the subterranean formation may be an indication that the produced fluid originated from the corresponding zone. Detection of optical properties in the produced fluid that correspond to silica nanoparticles introduced into different zones may be an indication that the produced fluid comprises formation fluid originating from each of the corresponding zones.

Thus, for instance, a first fluid having fluorescent silica nanoparticles may be introduced into a first zone of a formation. A second fluid having qualitatively distinguishable silica nanoparticles from the fluid introduced into the first zone may be introduced into a second zone of a formation. A proportion of formation fluid originating from each zone may be determined by, for example, the relative value or intensity of the corresponding measured optical property in the formation fluid.

As one non-limiting example, a first group of silica nanoparticles exhibiting a first optical property may be introduced into a first zone, and at least a second group of silica nanoparticles exhibiting a second optical property may be introduced into a second zone. An absorption spectrum, an emission spectrum or other optical property of produced fluids may be measured to determine if any of the first group of silica nanoparticles or the second group of silica nanoparticles are present in the produced fluid. For example, an emission spectrum of the produced fluid may be used to determine a proportion of the produced fluid that originated from each zone based on the fluorescence intensity of the silica nanoparticles introduced into each zone.

In addition to monitoring different zones in hydrocarbon production wells and determining the zone in which hydrocarbons have been produced from the formation, the silica nanoparticles may also be used to monitor oil and gas for flow assurance and for maintaining regulatory compliance. The ability to analyze the fluids on-site, quickly and frequently, further assists operators to detect flow assurance, asset integrity and process problems early enabling them to take preventative action to minimize the risks of production loss and to adapt the treatment operation.

Further, the silica nanoparticles may also be used to determine sites of flowback water and produced water as well as for detection or early warning of phenomena such as water breakthrough.

The silica nanoparticles may be introduced into an injection fluids during at least one of water flooding, steam assisted gravity drainage, steam flooding, cyclic steam stimulation, or other enhanced oil recovery stimulation processes to determine fluid flow paths through the subterranean formation and into produced fluids.

In other embodiments, different silica nanoparticles are preferably introduced into the aqueous fluid introduced into the different injection wells. Fluids produced from one or more production wells may be analyzed for the presence of the silica nanoparticles in the produced fluid. The presence of silica nanoparticles in produced fluids from a production well may indicate water breakthrough. Thus, not only can water breakthrough in the production well be determined but the injection well from which the water has flowed in into the production well can be identified. The injection well, into which the water in the breakthrough water has been determined to have been initially introduced, can be shut off. Thus, the silica nanoparticles can be used to optimize enhancement of hydrocarbons during secondary recovery operations by shutting down the injection well and thus terminating the flow of water from the injection well directly into the production well.

The silica nanoparticles used in this embodiment are typically water dispersible. Silica nanoparticles are introduced into the aqueous fluid which is then introduced into the injection well. The aqueous fluid introduced into each of the injection wells contains qualitatively distinguishable silica nanoparticles. The aqueous fluid serves to maintain pressure in the hydrocarbon-bearing reservoir. The pressure is maintained above the bubble point. Should silica nanoparticles be detected in produced fluid from the production well, the operator would know to take remedial action and shut down the injection well from which the silica nanoparticles had originally been introduced. The injection well, once shut down, may be repaired to prevent further flow of aqueous fluid into the production well.

Information about the wettability of the formation surfaces may be particularly useful where stimulation methods include expensive fluids, such as those including surfactants, micellar fluids, or polymers. Where the formation includes more water wet surfaces than oil wet surfaces, an aqueous-based stimulation fluid may be used during further stimulation procedures. Where the formation includes more oil wet surfaces than water wet surfaces, a non-polar stimulation fluid may be used during further stimulation procedures.

In some embodiments, a mixture of hydrophilic and hydrophobic silica nanoparticles exhibiting different optical properties may be introduced into the subterranean formation, into the production well or into one or more injection wells.

A ratio of hydrophilic silica nanoparticles to hydrophobic silica nanoparticles in a produced fluid may be determined by an optical property of the produced fluid. The ratio may be employed as an indication of a wettability of surfaces of the subterranean formation (e.g., a ratio of water wet surfaces to oil wet surfaces in the subterranean formation). It may also be indicative of the productivity of particular zones within the formation.

The silica nanoparticles may also be used to sweep a production well in an enhanced oil recovery (EOR) operation, such as flooding. Silica nanoparticles may be introduced into injection fluid and the injection fluid is then introduced into the formation. The injection fluid may be introduced by being pumped into one or more injection wells. Typically, the silica nanoparticles are dispersible in the delivery fluid.

The detection of the silica nanoparticles in fluids produced from the production well is indicative that the sweep, i.e., removal of the oil from pore spaces within the formation, has been completed.

In some embodiments, the silica nanoparticles may be introduced into the subterranean formation during stimulation processes. Stimulation processes such as, for example, hydraulic fracturing (i.e., "fracing") may be used to enhance hydrocarbon recovery from a hydrocarbon-bearing subterranean formation. In hydraulic fracturing operations, hydraulic fractures may be created or enlarged by injecting a fluid containing additives and including a suspended proppant material (e.g., sand, ceramics, etc.) into a targeted subterranean formation under elevated pressure conditions sufficient to cause the hydrocarbon-bearing formation material to fracture. The silica nanoparticles may be included in the fracturing fluid. Thus, in an embodiment, a method of fracturing multiple zones of a subterranean formation penetrated by a well comprises: pumping into each zone of the formation to be fractured a fracturing fluid, wherein the fracturing fluid pumped into each zone comprises a qualitatively distinguishable tracer comprising silica nanoparticles which are either hydrocarbon soluble, water soluble or both hydrocarbon soluble and water soluble; enlarging or creating a fracture in the formation; recovering fluid from at least one of the multiple zones; and identifying the zone within the subterranean formation from which the recovered fluid was produced by identifying the silica nanoparticles in the recovered fluid. In another embodiment, a method of monitoring the production of fluids produced in multiple productive zones of a subterranean formation penetrated by a well comprises pumping fracturing fluid into the multiple productive zones at a pressure sufficient to enlarge or create fractures in each of the multiple productive zones, wherein the fracturing fluid comprises fluorescent silica nanoparticles which are either hydrocarbon soluble, water soluble or both hydrocarbon soluble and water soluble and further wherein the fluorescent silica nanoparticles pumped into each of the multiple productive zones is qualitatively and/or quantitatively distinguishable; and monitoring the amount of fluids produced from at least one of the multiple productive zones from the silica nanoparticles in the produced fluid.

In addition to their use in hydraulic fracturing, the silica nanoparticles may be included in fluids used in well treating applications near wellbore and may be directed toward improving wellbore productivity and/or controlling the production of formation sand. Particular examples include gravel packing and "frac-packs." Typical gravel packing and frac packing methods.

In gravel packing, sand is used to pre-pack a screen to prevent the passage of formation particles or unconsolidated materials from the formation into the wellbore during production of fluids from the formation. Gravel packing is essentially a technique for building a two-stage filter downhole. The filter consists of gravel pack sand and a screen or liner. The gravel pack sand is sized according to the particle size distribution of the unconsolidated materials. The screen or liner has openings that are sized to retain the gravel pack sand. Thus the gravel pack particulates retain the unconsolidated formation materials and the screen or liner retains the gravel pack particulates. The gravel pack particulates and the screen or liner act together to reduce or eliminate the production of the unconsolidated formation materials with the oil or gas production. A slurry of sand introduced into the well further may contain the silica nanoparticles. The slurry is then pumped into the workstring within the well until the slurry is within about 150 to about 300 feet of the primary port. Positioning of a crossover service tool allows the slurry to travel into the screen/casing annulus. Particulates are retained by the screen or liner and the remaining fluid leaks off into the formation allowing a tightly packed sand filter to remain in place. Monitoring the silica nanoparticles provides information of the type and amount of the produced fluid from the formation.

The silica nanoparticles may further be used in a frac pack operation where the unconsolidated formation is hydraulically fractured while a two-stage filter of gravel pack is simultaneously built. In frac packing, the processes of hydraulic fracturing and gravel packing are combined into a single treatment to provide stimulated production and an annular gravel pack to reduce formation sand production.

EXPERIMENTAL

Synthesis of Silica Nanoparticle ($SiO_2$)

Figure 4:
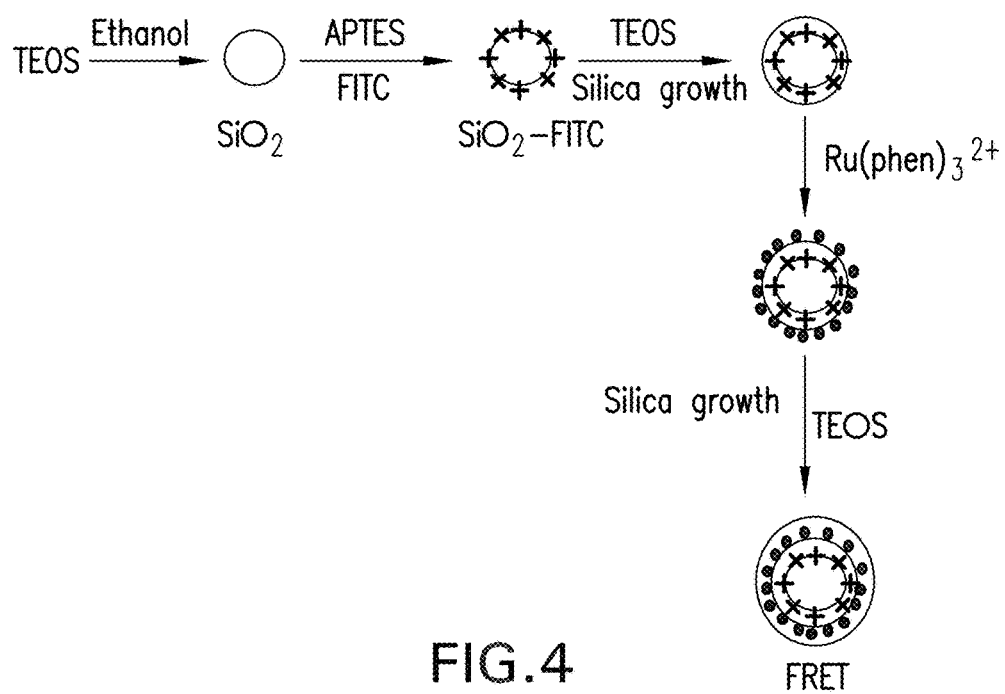
FIG. 4 is a schematic representation of the synthesis of a specific example of silica nanoparticles according to an embodiment of the disclosure.
Figure 5A:
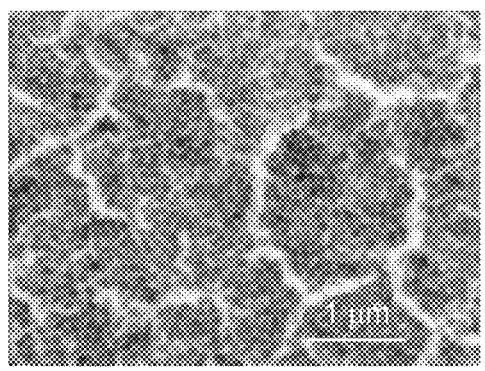
FIG. 5 shows SEM images of synthesized silica with low (A) and high magnification (B) and FRET-silica with low (C) and high magnification (D)
Figure 5B:
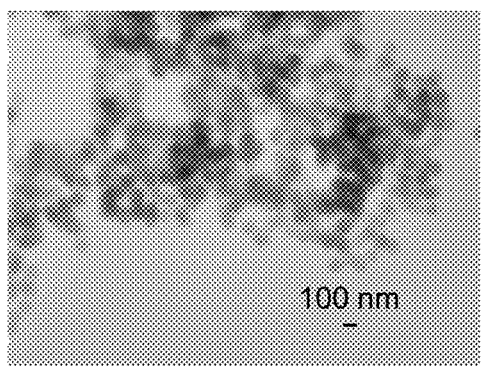
Figure 5C:
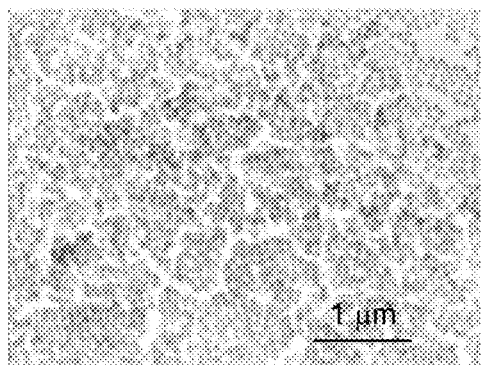
Figure 5D:
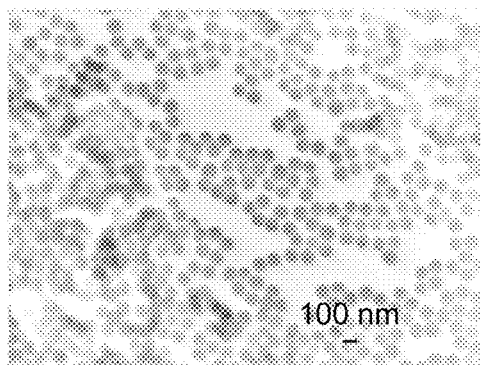

Silica nanoparticles were prepared by sol-gel process using ammonia and water as catalysts by utilizing the modified Stöber synthesis method (Stöber and Fink, 1968; Xu et al. 2010). Schematic representation of overall synthetic process is shown in FIG. 4.

About 2.5 mL of tetraethyl ortho silicate (TEOS) was added to 100 mL ethanol solution containing ammonia (4 mL) and water (2 mL). The reaction mixture was kept under stirring at 50° C. for 3 h and the 0.04 mL of (3-Aminopropyl) triethoxysilane (APTES) was added and the reaction was continued for another 3 h under stirring at 50° C. Then the reaction mixture was centrifuged at 4000 rpm for 10 mins to collect the silica nanoparticles modified with APTES. The separated particles were washed 3 times to remove unreacted chemicals and then dispersed in 100 mL ethanol.

Synthesis of $SiO_2$-Dye1-$SiO_2$

Dye 1 (fluorescein isothiocyanate (FITC), 30 µmol concentration) was added to 100 mL ethanol containing silica nanoparticles, mixed and stirred at 40° C. for 18 h, after which the particles were isolated by centrifugation and washed several times with ethanol to remove free dyes present in the solution. Then the particles were dispersed in 100 mL of ethanol.

To that dispersion about 1.85 mL TEOS, 1.2 mL ammonia and 0.7 mL water was added and allowed to grow a shell over the dye-1 adsorbed silica particle. Then the reaction mixture was centrifuged at 4000 rpm for 10 mins to collect the silica nanoparticles. The separated particles were washed 3 times to remove unreacted chemicals; and then dispersed in 100 mL ethanol. No emission of dye was observed in the supernatant liquid after several wash.

Synthesis of $SiO_2$-Dye1-$SiO_2$-Dye2-Silica (FRET or FRET-Silica)

To 20 mL of the above dispersion, 6 µmol concentration of dye 2 ((tris (1,10-phenanathroline) ruthenium) was added and the solution was diluted to a total volume of 32 mL. After stirring for 10 mins, about 0.25 mL TEOS, 0.2 mL ammonia, and 0.1 mL water were added; and the reaction mixture was stirred at room temperature. After 3 h, the reaction mixture was centrifuged; and the resulting particles were washed several times to remove unreacted chemicals. No emission of dye was observed in the supernatant liquid after several wash; and then the particles were dispersed in 10 mL ethanol. Similarly other concentrations were made using 12, 17 and 22 µmols of dye 2.

Functionalization of FRET-Silica

To 15 mL of ethanol, 10 mg of FRET-silica particles were added and dispersed well by sonication, after which 0.2 mL of hexadecyltrimethoxy silane (HDTMS) was added. The solution was stirred for 2 h at room temperature and then the solution was centrifuged using ethanol to remove the unreacted reactant and to separate the functionalized nanoparticles. The separated functionalized FRET-silica nanoparticles were dried in the oven at 60° C. and used for characterization.

Synthesized and functionalized silica nanoparticles were analyzed by scanning electron microscopy (SEM) using a field emission scanning electron microscope—JEOL JSM-7800. Fluorescence measurements were obtained using Horiba Jobin Yvon Fluorolog 3 spectrofluorometer equipped with a single grating monochromator and a photomultiplier tube detector having an accuracy of 0.5 nm.

FTIR was performed by ATR mode using Thermo Fisher with use of Germanium ATR. The samples placed over the Germanium ATR and the measurements were performed for 128 scans with the resolution of 4 $cm^{-1}$.

Results and Discussion

Synthesized silica nanoparticles were characterized by different spectroscopic techniques. FIGS. 5 A & B shows the lower and higher magnification SEM images of as synthesized particles having spherical morphology and a particle size between 50-100 nm. FIGS. 5 C & D shows the lower and higher SEM image of FRET-silica with higher loading of about 22 µmols of dye 2 (acceptor). The analysis shows that the particle size does not change with increase in the concentration of acceptor molecules.

Figure 6:
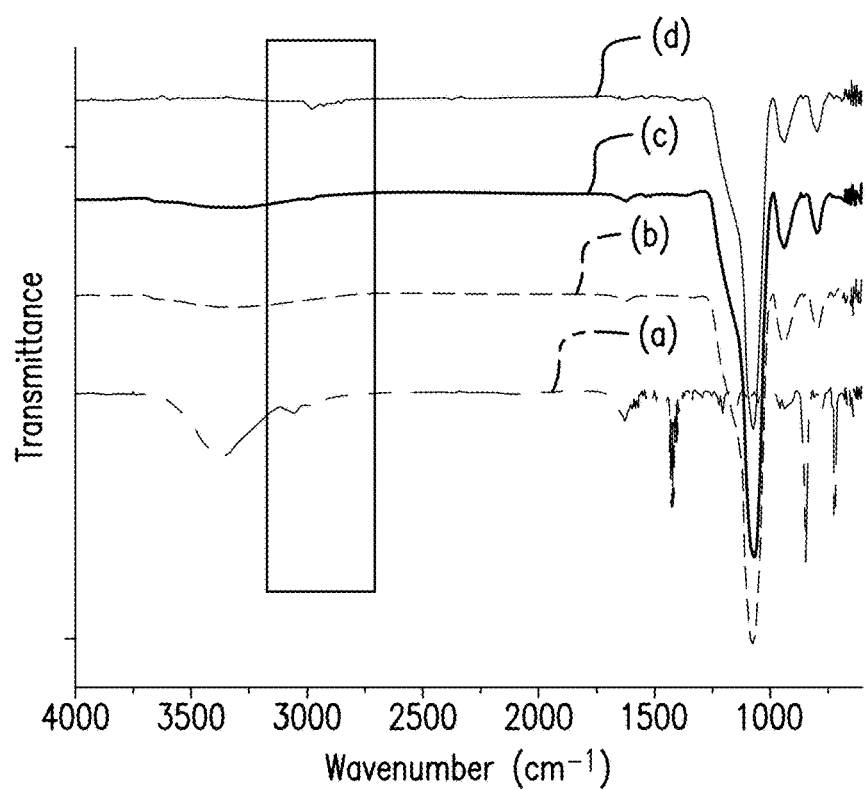
FIG. 6 shows FT-IR spectrum of Ru (phen)$_3$ ion complex (dye-2) (a), silica with dye-1 (b), FRET-silica (c), and functionalized FRET-silica (d)

Silica nanoparticles have been further characterized with FT-IR spectroscopy in ATR mode. FIG. 6 shows FT-IR spectra of Ru (phen)$_3$ ion complex (dye-2) (a), silica with dye-1 (b), FRET-silica (c) and functionalized FRET-silica (d). The presence of Si—O—Si and Si—O—C characteristic bands was found around 1095 and 1110 $cm^{-1}$ respectively in the samples of silica-dye-1 and FRET-silica. These bands become predominant and mask the fingerprint region of the dyes to a very great extent. Further after functionalization, the FRET-silica shows the presence of organic stretching frequencies around 2919 and 2846 $cm^{-1}$ in FIG. 6d, which correspond to the —$CH_2$— anti symmetric and symmetric stretching of HDTMS. Peak at 1460 $cm^{-1}$ corresponds to bending vibrations of the —$CH_2$— groups. Presence of these groups in the functionalized silica confirms that the functionalization process was successful.

Figure 7:
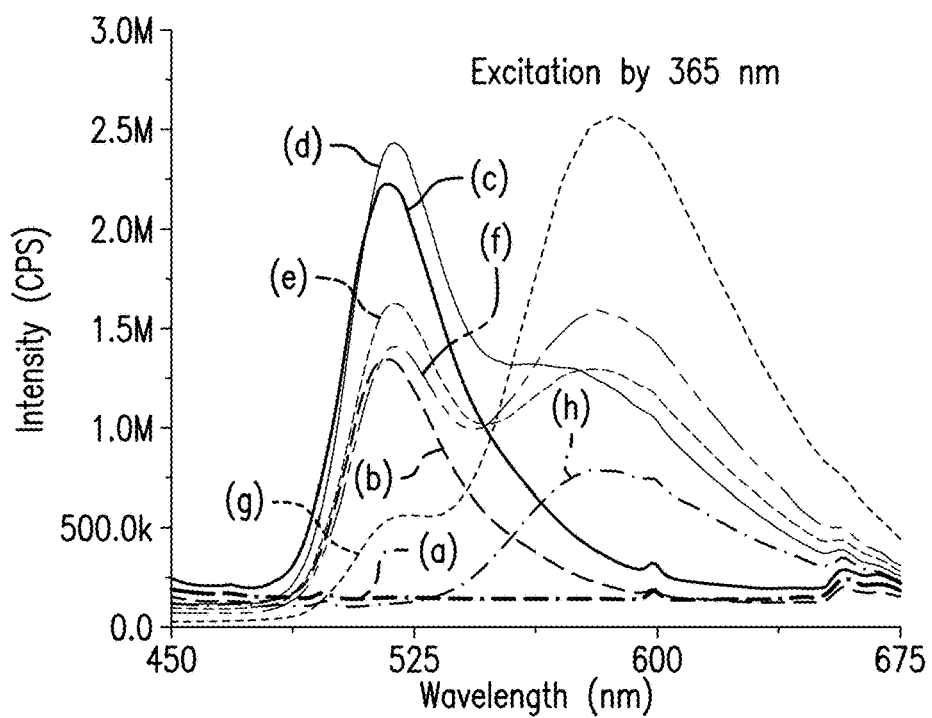
FIG. 7 shows fluorescence emission spectrum of all the samples with excitation at 365 nm, wherein (a) is as synthesized silica nanoparticles without any dye, (b) is silica-dye-1, (c) is $SiO_2$-dye-1-$SiO_2$, (d), (e), and (f) are FRET-silica having 6, 12, 17, and 22 μmols of dye-2 respectively, and (h) is silica matrix alone with high concentration of dye-2 (about 42 μmols)

Fluorescence measurements were performed with the silica nanoparticle dispersed in de-ionized water taken in a quartz cuvette and by excitation by 365 nm. FIG. 7 shows the emission spectra of all the samples. As synthesized silica nanoparticles without any dye has no emission spectrum (a), with the addition of dye-1 to silica particles there is a sharp emission around 520 nm (b). Further coating the silica-dye 1 with another layer of silica shows the same peak around 520 nm (c). However, the intensity of the peaks is increased with the addition of the silica layer. This further confirms that silica plays an important role in enhancing the quantum efficacy of the emission process. In order to introduce FRET in the system, dye-2 (acceptor) was added in different concentrations. Addition of dye-2 to the system further enhances an additional peak around 600 nm for all the concentrations such as 6, 12, 17, and 22 µmols (See FIG. 7 graph d, e, f and g). In addition, the peak intensity increases when the concentration of dye 2 increases. This increase in the intensity and the peak shift lead to multicolor property. Silica matrix alone with high concentration of dye-2 about 42 µmols shows emission peak around 600 nm with 365 nm excitation (graph h). However, the single intensity is lower when it is compared to the FRET-silica with various concentration of dye-2. The energy transfer from dye-1 to dye-2 plays an important role in fluorescence enhancement in FRET-silica nanoparticles.

Figure 8:
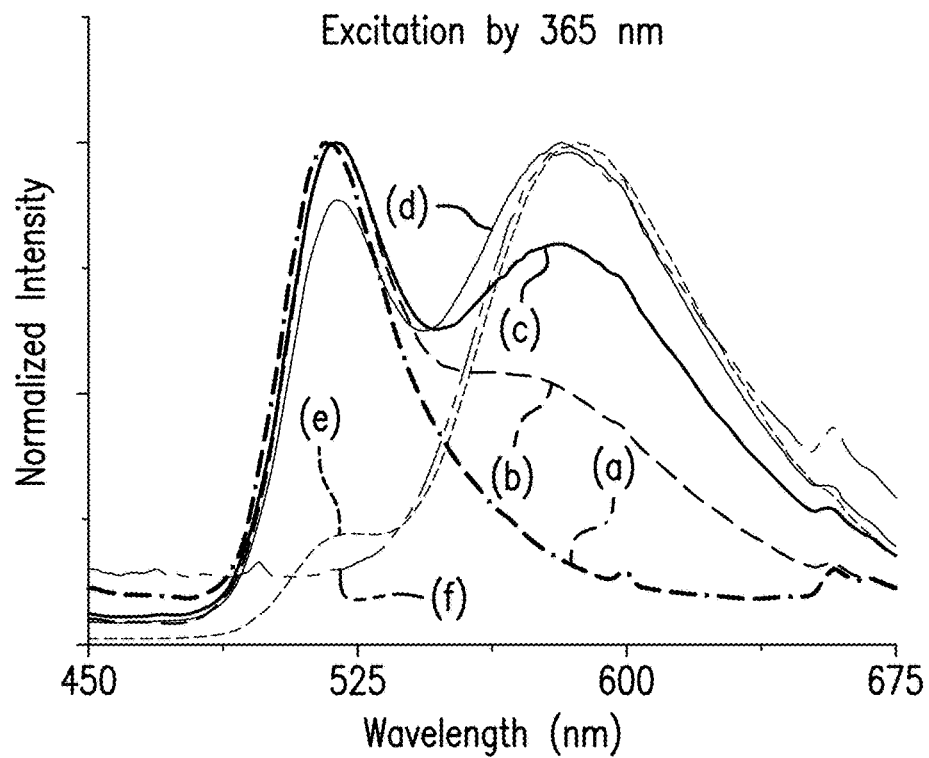
FIG. 8 is normalized fluorescence emission spectrum of all the samples with excitation at 365 nm, wherein (a) is silica-dye-1, (b) is FRET-silica with 6 μmols of dye-2, (c) is FRET-silica with 12 μmols of dye-2, (d) is FRET-silica with 17 μmols of dye-2, (e) is FRET-silica with 22 μmols of dye-2, and (f) is silica with 42 μmols of dye-2 alone.

Fluorescence spectra of all the samples in the deionized water was normalized with respect to maximum intensity to find the variation with respect to concentration of dye-2 and shift in the wavelength (FIG. 8). From the analysis it shows that there is a concentration dependence with intensity of peak around 600 nm and also there is a shift in wavelength.

Figure 9:
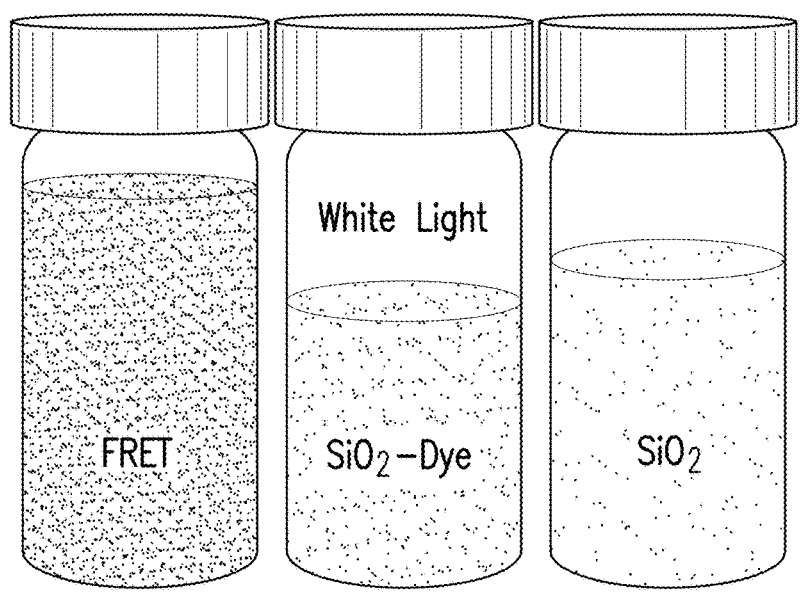
FIG. 9 is a photograph of as synthesized silica, dye-1 incorporated silica, and FRET silica samples exposure to white light.
Figure 10:
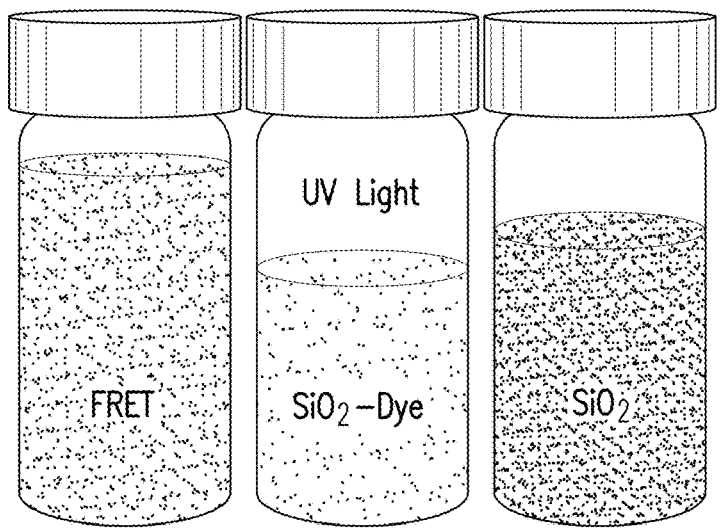
FIG. 10 is a photograph of as synthesized silica, dye-1 incorporated silica, and FRET silica samples exposure to UV light.

Photographic pictures were taken in white light (FIG. 9) and UV-light (FIG. 10) to see the color difference with as synthesized silica, dye-1 incorporated silica and FRET silica with 22 µmols of dye-2. FIG. 10 shows the color difference in UV light due to the fluorescence property of the molecules (donor and acceptors).

Figure 11:
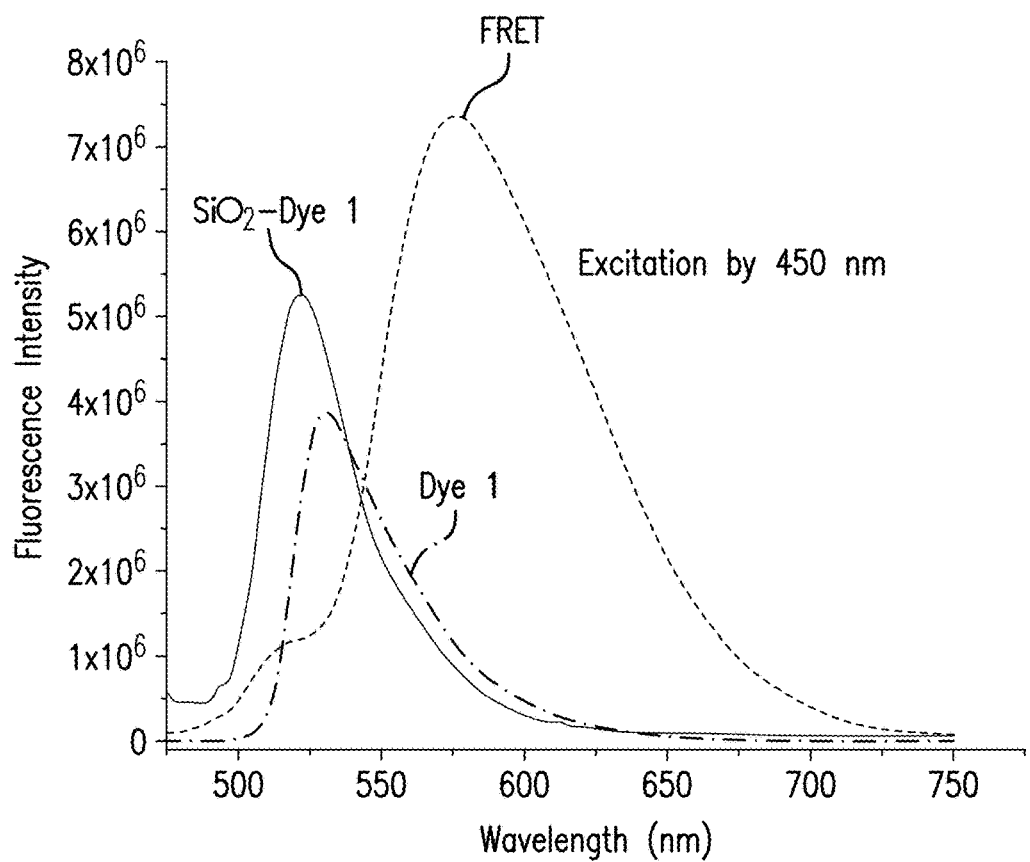
FIG. 11 shows fluorescence emission spectra at 450 nm excitation.

Different wavelengths for excitation were screened. The optimum wavelength for the excitation was chosen to be 450 nm, in order to avoid direct excitation of the acceptors to maximize the FRET. FIG. 11 shows the fluorescence emission spectra at 450 nm excitation. From the analysis it clearly shows that the interaction of dye-1 with silica enhances its fluorescence intensity; and also there is a blue shift in the wavelength. Further with the FRET-silica of higher concentration of acceptor we can clearly see the drastic increase in the fluorescence intensity and shift in the spectrum towards red region. This is due to dye-dye interaction and facile energy transfer process in silica.

Figure 12:
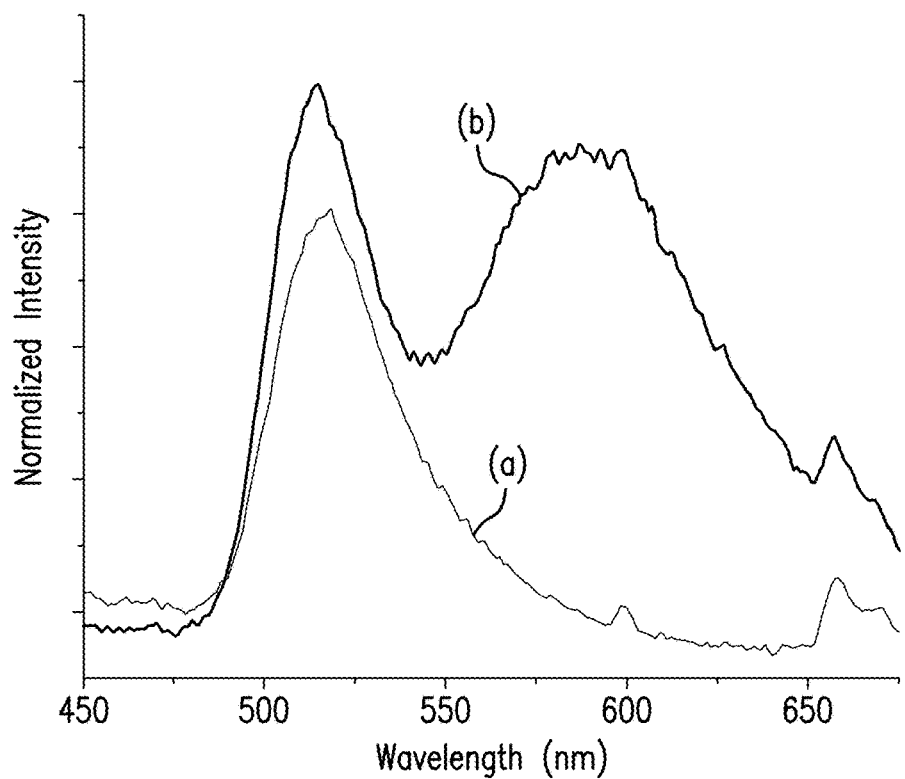
FIG. 12 shows fluorescence emission spectra of silica with dye-1 and FRET silica nanoparticle by excitation at 365 nm.

The stability of silica with dye-1 and FRET-silica nanoparticles were tested in API brine solution at 80° C. for 24 h. Detailed fluorescence activity was studied by analyzing the emission spectra from the samples with excitation at 365 nm (FIG. 12). The observed fluorescence signatures are comparable with the spectra of the corresponding nanoparticles in the deionized water, which shows that the FRET-silica are stable in API brine at elevated temperatures for an extended period of time.

Figure 13:
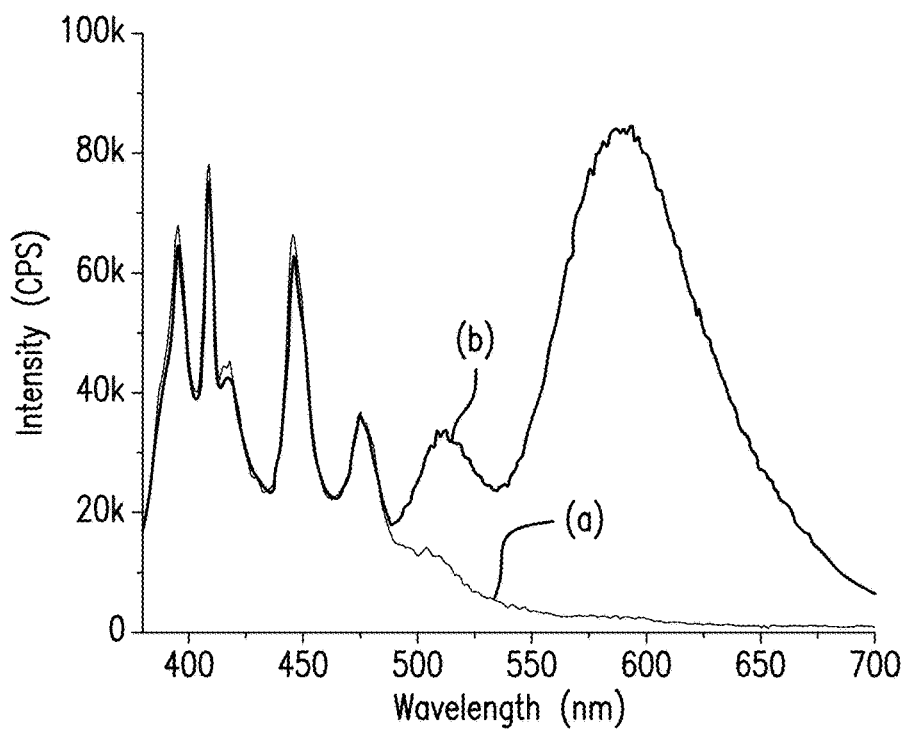
FIG. 13 shows emission spectra of mineral oil (a) and FRET-silica dispersed in mineral oil (b) by excitation at 365 nm.

Functionalized FRET silica were dispersed in mineral oil for fluorescence activity measurement. Functionalized silica nanoparticles show very good dispersion in the oil. The spectra were generated by exciting the samples at 365 nm wavelength. FIG. 13 shows the emission spectrum of mineral oil and functionalized FRET silica in mineral oil. From the analysis of the spectrum it clearly shows the distinct peaks pertaining to the FRET. Generally, the mineral oil shows peaks in the low wavelength region with excitation.

Time resolved fluorescence measurement was performed to obtain the information about the lifetime. Fluorescence lifetime provides the absolute measure which is independent of concentration whereas the steady state gives as an average and relative presentation. FIG. 14 shows the TCSPC (time correlated single photon counting) lifetime measurement of dye-1, dye-1 incorporated silica, and FRET-silica. It clearly shows that FRET-silica has longer life time than dye-1 incorporated silica and pure dye-1. This enhanced lifetime is due to the charge transfer from the donor to the acceptor.

The example has demonstrated that environmentally friendly silica nanoparticles as fluorescence tracer has been developed. Multicolor silica nanoparticles are generated through FRET mechanism of donor and acceptor dye molecules. Multicolor generation in these silica nanoparticles are through a single excitation wavelength with charge transfer from donor dye molecules to acceptor dye molecules. Unique method of synthesis makes the ingredients show enhanced fluorescence signal. The enhancement in the signal is mainly due to the presence of dielectric silica that facilitates the charge transfer process. Due to the FRET effect, FRET-silica nanoparticles exhibit longer lifetime. Hydroxyl groups in the FRET-silica nanoparticles help to further functionalize the nanoparticles towards oil dispersibility. Further the FRET-silica nanoparticles can be used for the dual purpose of tracers and oil recovery enhancement agent. The environmentally friendly multicolor silica nanoparticles can facilitate in-situ monitoring of reservoir communication thus improving oil production.

Set forth are various embodiments of the disclosure.

Embodiment 1

A method of determining a property within a subterranean formation, the method comprising: introducing silica nanoparticles into a well; obtaining a sample of a fluid produced from the well; and analyzing the sample for presence of the silica nanoparticles, wherein the silica nanoparticles comprise a core, a donor chromophore, an acceptor chromophore, and an outer silica shell; the donor chromophore and the acceptor chromophore being selected such that an emission spectrum of the donor chromophore overlaps with an absorption spectrum of the acceptor chromophore.

Embodiment 2

The method of Embodiment 1, wherein the silica nanoparticles are included in a fluid, and the method comprises injecting the fluid into the well.

Embodiment 3

The method of Embodiment 1 or Embodiment 2, wherein the fluid is injected into the well during a fracturing operation, a sand control operation, a flooding operation, an acidifying operation, or a combination comprising at least one of the foregoing.

Embodiment 4

The method of any one of Embodiments 1 to 3, further comprising: introducing silica nanoparticles exhibiting a first optical property into a first zone of the well; introducing silica nanoparticles exhibiting second optical property into a second zone of the well; and analyzing the sample for presence of silica nanoparticles exhibiting the first optical property and the silica nanoparticles exhibiting the second optical property.

Embodiment 5

A method of fracturing multiple productive zones of a subterranean formation penetrated by a well, the method comprising: injecting a fracturing fluid into the multiple production zones at a pressure sufficient to enlarge or create fractures in the multiple productive zones, wherein the fracturing fluid comprises silica nanoparticles; recovering a fluid containing hydrocarbons from one or more of the multiple productive zones; detecting the silica nanoparticles in the recovered fluid; and identifying the zone from which the recovered fluid was produced from which the recovered fluid was produced by identifying the silica nanoparticles in the recovered fluid, wherein the silica nanoparticles comprise a core, a donor chromophore, an acceptor chromophore, and an outer silica shell; the donor chromophore and the acceptor chromophore being selected such that an emission spectrum of the donor chromophore overlaps with an absorption spectrum of the acceptor chromophore.

Embodiment 6

A method of monitoring the production of fluids produced in multiple productive zones of a subterranean formation penetrated by a well comprises pumping fracturing fluid into the multiple productive zones at a pressure sufficient to enlarge or create fractures in each of the multiple productive zones, wherein the fracturing fluid comprises fluorescent silica nanoparticles which are either hydrocarbon soluble, water soluble or both hydrocarbon soluble and water soluble and further wherein the fluorescent silica nanoparticles pumped into each of the multiple productive zones is qualitatively and/or quantitatively distinguishable; and monitoring the amount of fluids produced from at least one of the multiple productive zones from the silica nanoparticles in the produced fluid, wherein the silica nanoparticles comprise a core, a donor chromophore, an acceptor chromophore, and an outer silica shell; the donor chromophore and the acceptor chromophore being selected such that an emission spectrum of the donor chromophore overlaps with an absorption spectrum of the acceptor chromophore.

Embodiment 7

The method of Embodiment 6, further comprising determining the presence of dispersed oil in produced water from the silica nanoparticles.

Embodiment 8

The method of any one of Embodiments 5 to 7, wherein the silica nanoparticles injected into each of the multiple productive zones is qualitatively distinguishable, quantitatively distinguishable, or a combination thereof.

Embodiment 9

A method of enhancing the production of hydrocarbon from a production well penetration a hydrocarbon bearing formation, wherein one or more of the injection well are associated with the production well, the method comprising: introducing into one or more of the injection wells a fluid comprising silica nanoparticles; flowing at least a portion of the fluid comprising the silica nanoparticles from the injection well to the production well; and recovering a production fluid from the production well, wherein the silica nanoparticles comprise a core, a donor chromophore, an acceptor chromophore, and an outer silica shell; the donor chromophore and the acceptor chromophore being selected such that an emission spectrum of the donor chromophore overlaps with an absorption spectrum of the acceptor chromophore.

Embodiment 10

A method of determining water breakthrough in a production well associated with one or more injection wells, the method comprising: introducing a fluid comprising silica nanoparticles into an injection well; flowing the fluid from the injection well into the production well; producing a production fluid from the production well; determining water breakthrough in the production well by qualitatively determining the presence or quantitatively measuring the amount of the silica nanoparticles in the production fluid, wherein the silica nanoparticles comprise a core, a donor chromophore, an acceptor chromophore, and an outer silica shell; the donor chromophore and the acceptor chromophore being selected such that an emission spectrum of the donor chromophore overlaps with an absorption spectrum of the acceptor chromophore.

Embodiment 11

A method of increasing hydrocarbon production from a production well penetrating a hydrocarbon-bearing reservoir, wherein more than one injection well is associated with the production well, the method comprising: injecting a fluid comprising functionalized silica nanoparticles into the more than one injection well, the fluid pumped into each of the injection wells comprising qualitatively distinguishable silica nanoparticles; identifying, upon water breakthrough in the production well, the injection well into which the breakthrough water was injected by qualitatively determining the presence of silica nanoparticles hydrocarbons recovered from the production well; and shutting off the identified injection well, wherein the silica nanoparticles comprise a core, a donor chromophore, an acceptor chromophore, and an outer silica shell; the donor chromophore and the acceptor chromophore being selected such that an emission spectrum of the donor chromophore overlaps with an absorption spectrum of the acceptor chromophore.

Embodiment 12

The method of any one of Embodiments 1 to 11, wherein the core comprises silica.

Embodiment 13

The method of Embodiment 12, wherein the core is doped with the donor chromophore via coating, adsorption, absorption, covalent bonding, or a combination comprising at least one of the foregoing.

Embodiment 14

The method of any one of Embodiments 1 to 13, wherein the silica nanoparticles further comprise an intermediate silica shell encapsulating the core and the donor chromophore.

Embodiment 15

The method of Embodiment 14, wherein the intermediate silica shell is doped with the acceptor chromophore via coating, adsorption, absorption, covalent bonding, or a combination comprising at least one of the foregoing.

Embodiment 16

The method of any one of Embodiments 1 to 15, wherein the donor chromophore is a fluorescent and the acceptor chromophore is a fluorescent or phosphorescent.

Embodiment 17

The method of any one of Embodiments 1 to 16, wherein the outer silica shell is functionalized.

All ranges disclosed herein are inclusive of the endpoints, and the endpoints are independently combinable with each other. "Or" means "and/or." All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. The modifier "about" used in connection with a quantity is inclusive of the stated value and has the meaning dictated by the context (e.g., it includes the degree of error associated with measurement of the particular quantity).

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method of determining a property within a subterranean formation, the method comprising:
   introducing silica nanoparticles into a well;
   obtaining a sample of a fluid produced from the well; and
   analyzing the sample for presence of the silica nanoparticles,
   wherein the silica nanoparticles comprise a silica core, a donor chromophore, an acceptor chromophore, and an outer silica shell;
   the donor chromophore and the acceptor chromophore being selected such that an emission spectrum of the donor chromophore overlaps with an absorption spectrum of the acceptor chromophore.

2. The method of claim 1, wherein the silica core is doped with the donor chromophore via coating, adsorption, absorption, covalent bonding, or a combination comprising at least one of the foregoing.

3. The method of claim 2, wherein the silica nanoparticles further comprise an intermediate silica shell encapsulating the silica core and the donor chromophore.

4. The method of claim 3, wherein the intermediate silica shell is doped with the acceptor chromophore via coating, adsorption, absorption, covalent bonding, or a combination comprising at least one of the foregoing.

5. The method of claim 1, wherein the donor chromophore is a fluorescent and the acceptor chromophore is a fluorescent or phosphorescent.

6. The method of claim 1, wherein the outer silica shell is functionalized.

7. The method of claim 1, wherein the silica nanoparticles are included in a fluid, and the method comprises injecting the fluid into the well.

8. The method of claim 1, wherein the fluid is injected into the well during a fracturing operation, a sand control operation, a flooding operation, an acidifying operation, or a combination comprising at least one of the foregoing.

9. The method of claim 1, further comprising:
   introducing silica nanoparticles exhibiting a first optical property into a first zone of the well;
   introducing silica nanoparticles exhibiting second optical property into a second zone of the well; and
   analyzing the sample for presence of silica nanoparticles exhibiting the first optical property and the silica nanoparticles exhibiting the second optical property.

10. The method of claim 1, wherein the donor chromophore is present in an amount of about 0.1 micro moles to about 10 milli moles, and the acceptor chromophore is present in an amount of about 0.001 micromoles to about 10 milli moles, each based on 1 gram of the silica core.

11. The method of claim 1, wherein the donor chromophore is present in an amount of about 1 micro moles to about 10 milli moles, and the acceptor chromophore is present in an amount of about 0.01 micro moles to about 10 milli moles, each based on 1 gram of the silica core.

12. The method of claim 1, wherein the donor chromophore comprises fluorescein isothiocyanate and the acceptor chromophore comprises tris(1,10-phenanathroline) ruthenium.

13. A method of fracturing multiple productive zones of a subterranean formation penetrated by a well, the method comprising:
   injecting a fracturing fluid into the multiple production zones at a pressure sufficient to enlarge or create fractures in the multiple productive zones, wherein the fracturing fluid comprises silica nanoparticles;
   recovering a fluid containing hydrocarbons from one or more of the multiple productive zones;
   detecting the silica nanoparticles in the recovered fluid; and
   identifying the zone from which the recovered fluid was produced or monitoring an amount of fluids produced from at least one of the multiple productive zones by identifying the silica nanoparticles in the recovered fluid,
   wherein the silica nanoparticles comprise a silica core, a donor chromophore, an acceptor chromophore, and an outer silica shell;
   the donor chromophore and the acceptor chromophore being selected such that an emission spectrum of the donor chromophore overlaps with an absorption spectrum of the acceptor chromophore.

14. The method of claim 13, further comprising determining the presence of dispersed oil in produced water from the silica nanoparticles.

15. The method of claim 13, wherein the silica nanoparticles injected into each of the multiple productive zones is qualitatively distinguishable, quantitatively distinguishable, or a combination thereof.

16. A method of enhancing the production of hydrocarbon from a production well penetration a hydrocarbon bearing formation, wherein one or more of the injection well are associated with the production well, the method comprising:
   introducing into one or more of the injection wells a fluid comprising silica nanoparticles;
   flowing at least a portion of the fluid comprising the silica nanoparticles from the injection well to the production well; and
   recovering a production fluid from the production well,
   wherein the silica nanoparticles comprise a silica core, a donor chromophore, an acceptor chromophore, and an outer silica shell;
   the donor chromophore and the acceptor chromophore being selected such that an emission spectrum of the donor chromophore overlaps with an absorption spectrum of the acceptor chromophore.

17. The method of claim 16, wherein the donor chromophore is a fluorescent and the acceptor chromophore is a fluorescent or phosphorescent.

18. The method of claim 16, wherein the silica nanoparticles are functionalized.

19. A method of determining water breakthrough in a production well associated with one or more injection wells, the method comprising:
   introducing a fluid comprising silica nanoparticles into an injection well;
   flowing the fluid from the injection well into the production well;
   producing a production fluid from the production well;
   determining water breakthrough in the production well by qualitatively determining the presence or quantitatively measuring the amount of the silica nanoparticles in the production fluid,
   wherein the silica nanoparticles comprise a silica core, a donor chromophore, an acceptor chromophore, and an outer silica shell;
   the donor chromophore and the acceptor chromophore being selected such that an emission spectrum of the donor chromophore overlaps with an absorption spectrum of the acceptor chromophore.

20. The method of claim 19, further comprising identifying, upon water breakthrough in the production well, the injection well into which the breakthrough water was injected by qualitatively determining the presence of silica nanoparticles in a fluid recovered from the production well.

21. The method of claim 20, further comprising shutting off the identified injection well.

22. The method of claim 19, wherein the donor chromophore is a fluorescent and the acceptor chromophore is a fluorescent or phosphorescent.

* * * * *